(12) United States Patent
Bergeron et al.

(10) Patent No.: US 7,279,028 B2
(45) Date of Patent: Oct. 9, 2007

(54) ELECTROSTATIC FILTER

(75) Inventors: Vance Bergeron, Francheville (FR); Laurent Adrien Fullana, L'etang la ville (FR)

(73) Assignee: Airinspace B.V., Delft (NL)

( * ) Notice: Subject to any disclaimer, the term of this patent is extended or adjusted under 35 U.S.C. 154(b) by 0 days.

(21) Appl. No.: 11/408,737

(22) Filed: Apr. 18, 2006

(65) Prior Publication Data

US 2007/0137486 A1    Jun. 21, 2007

Related U.S. Application Data

(60) Provisional application No. 60/751,497, filed on Dec. 17, 2005.

(51) Int. Cl.
*B03C 3/155* (2006.01)

(52) U.S. Cl. .............. 96/66; 55/518; 55/528; 55/DIG. 45; 96/69; 96/99

(58) Field of Classification Search .............. 96/66–69, 96/99; 55/518, 527, 528, DIG. 45
See application file for complete search history.

(56) References Cited

U.S. PATENT DOCUMENTS

| | | | | |
|---|---|---|---|---|
| 2,822,058 A | * | 2/1958 | Roos et al. ..................... | 96/66 |
| 3,509,696 A | * | 5/1970 | Thompson ..................... | 96/66 |
| 5,108,470 A | * | 4/1992 | Pick .............................. | 96/58 |
| 5,405,434 A | * | 4/1995 | Inculet ........................... | 96/54 |
| 5,474,600 A | * | 12/1995 | Volodina et al. ............... | 96/57 |
| 5,549,735 A | * | 8/1996 | Coppom ........................ | 96/63 |
| 5,573,577 A | * | 11/1996 | Joannou ........................ | 96/66 |
| 5,807,425 A | * | 9/1998 | Gibbs ............................ | 96/66 |
| 5,846,302 A | * | 12/1998 | Putro ............................. | 96/66 |
| 5,938,823 A | * | 8/1999 | Condit et al. .................. | 96/16 |
| 6,764,533 B2 | * | 7/2004 | Lobiondo, Jr. ................ | 96/66 |
| 6,805,732 B1 | * | 10/2004 | Billiotte et al. ............... | 96/66 |
| 6,901,808 B1 | * | 6/2005 | Sharpless et al. ............. | 73/724 |
| 7,041,780 B2 | * | 5/2006 | Buckley et al. ............. | 528/501 |
| 2003/0134416 A1 | * | 7/2003 | Yamanishi et al. .......... | 435/372 |
| 2005/0098040 A1 | * | 5/2005 | Billiotte et al. ............... | 96/15 |
| 2005/0132886 A1 | * | 6/2005 | Schultze et al. .............. | 96/66 |

FOREIGN PATENT DOCUMENTS

JP       53-112578    * 10/1978    ................ 96/66

* cited by examiner

*Primary Examiner*—Richard L. Chiesa
(74) *Attorney, Agent, or Firm*—Beyer Weaver LLP

(57) ABSTRACT

An electrostatic filter having an improved dielectric is described. The dielectric constitutes a dielectric mat formed from high porosity non-woven fibers having pores that have a void fraction of at least 97%. The dielectric mat is sandwiched by a pair of porous electrodes. The fibers that form the mat have a maximum cross sectional thickness that is less than 100 microns and a length to maximum thickness ratio of greater than 10. The pores are preferably statistically substantially equally sized and open in three dimensions. In various preferred embodiments, the void fraction of the dielectric mat is greater than 99 percent. The mat preferably has a tortuosity of at least 2. The maximal cross sectional width of the fibers is preferably in the range 0.1 to 50 microns. In many implementations, the fibers that form the dielectric mat are formed from either polyester or polypropylene. In some implementations, the cross section of the fibers will have at least one (and preferably two or more) distinct regions of small transversal radius of curvature along its perimeter.

19 Claims, 11 Drawing Sheets

ELECTROSTATIC FILTER

CROSS REFERENCE TO RELATED APPLICATION

This application claims priority benefit of U.S. Provisional Patent Application No. 60/751,497, filed Dec. 17, 2005, entitled "PLASMA BASED AIR PURIFICATION DEVICE," which is hereby incorporated herein by reference.

BACKGROUND OF THE INVENTION

The present invention generally relates to electrostatic filters. More particularly, the invention relates to dielectrics for use in electrostatic filters.

There are currently a wide range of technologies that are used to purify and/or filter air. One such technology is the electrostatic filter. Generally electrostatic filters include a porous dielectric material that is positioned between a pair of electrodes. A fluid stream (e.g., air) is arranged to pass through the dielectric material. In an active electrostatic filter, a significant potential difference is applied across the electrodes in order to induce an electrostatic field in the dielectric material that is sufficient to cause particulates within the air stream passing through the filter to adhere to the dielectric.

More recently, ion enhanced electrostatic filters have been developed. An ion enhanced electrostatic filter contemplates placing an ion source in front of the electrostatic filter to impart an electric charge to some of the particulates carried by air passing through the filter. The charges imparted to the particulates by the ionizer tend to help their collection within the dielectric.

U.S. Pat. No. 5,474,600, which is owned by the assignee of the present application, discloses an apparatus for the biological purification and filtration of air. Generally, the '600 patent discloses a system which utilizes a course electrostatic filter 1, a cylindrical or polygonal ionizer 5 and a fine electrostatic filter 10 that are all arranged in series. In some of the described embodiments, a pair of ionizers that impart opposite charges are arranged in series between the course and fine electrostatic filters. The system is arranged to inactivate (i.e. kill) biological objects (e.g., microorganisms and viruses) that are carried in the air stream and to filter particulates from the stream.

Commercial embodiments of this type of air purification and filtration system have been successfully used in the MIR space station and in hospitals to purify, filter and decontaminate air. A representative commercial embodiment of such a system is diagrammatically illustrated in FIG. 1. As seen therein, the system 20 include an electrostatic pre-filter 22, a positive plasma generator 24 that is arranged in series with a negative plasma generator 26 and a series of four electrostatic filters 28 that are arranged downstream of the negative plasma generator 26. Each D.C. plasma generator 24, 26 is composed of a plurality of cylindrical plasma cylinders (e.g., 6 cells) arranged in parallel. Each cell has a needle type ionizing electrode that is surrounded by a cylindrical electrode chamber. One of the electrodes is grounded while a D.C. potential of either 4000 or 7600 volts is applied to the opposing electrode. The electrostatic filters may be formed as described in U.S. Pat. No. 5,474,600 or 6,805,732 and plasma generator may be formed as described in U.S. Pat. No. 5,474,600 or U.S. Published Application No. 2005/0098040. All of these patents and patent applications are incorporated herein by reference.

Although the described system works well, there are continuing efforts to provide improved and/or more cost effective purification and/or filtering devices that can meet the needs of various applications.

SUMMARY OF THE INVENTION

In one aspect of the invention, an electrostatic filter having an improved dielectric is described. The dielectric constitutes a dielectric mat formed from high porosity non-woven fibers having pores that have a void fraction of at least 97% and a tortuosity of at least 1.7. The fibers have a maximum cross sectional thickness that is less than 100 microns and a length to maximum thickness ratio of greater than 10. In various preferred embodiments, the void fraction of the dielectric mat is greater than 99 percent. The pores are preferably statistically substantially equally sized and open in three dimensions. The various preferred embodiments, the tortuosity of the dielectric medium (mat) is at least 2 and more preferably at least 5.

The maximal cross sectional width of the fibers is preferably in the range 0.1 to 50 microns. In many implementations, the fibers that form the dielectric mat are formed from either polyester or polypropylene.

In some implementations, the cross section of the fibers will have at least one (and preferably two or more) distinct regions of small transversal radius of curvature along its perimeter.

The dielectric mat is sandwiched by a pair of porous electrodes. In some embodiments, one or both of the electrodes may be insulated.

BRIEF DESCRIPTION OF THE DRAWINGS

The invention, together with further objects and advantages thereof, may best be understood by reference to the following description taken in conjunction with the accompanying drawings in which.

It is to be understood that, in the drawings, like reference numerals designate like structural elements. It should also be understood that the depictions in the figures are diagrammatic and not to scale.

DETAILED DESCRIPTION OF THE PREFERRED EMBODIMENTS

Figure 1:
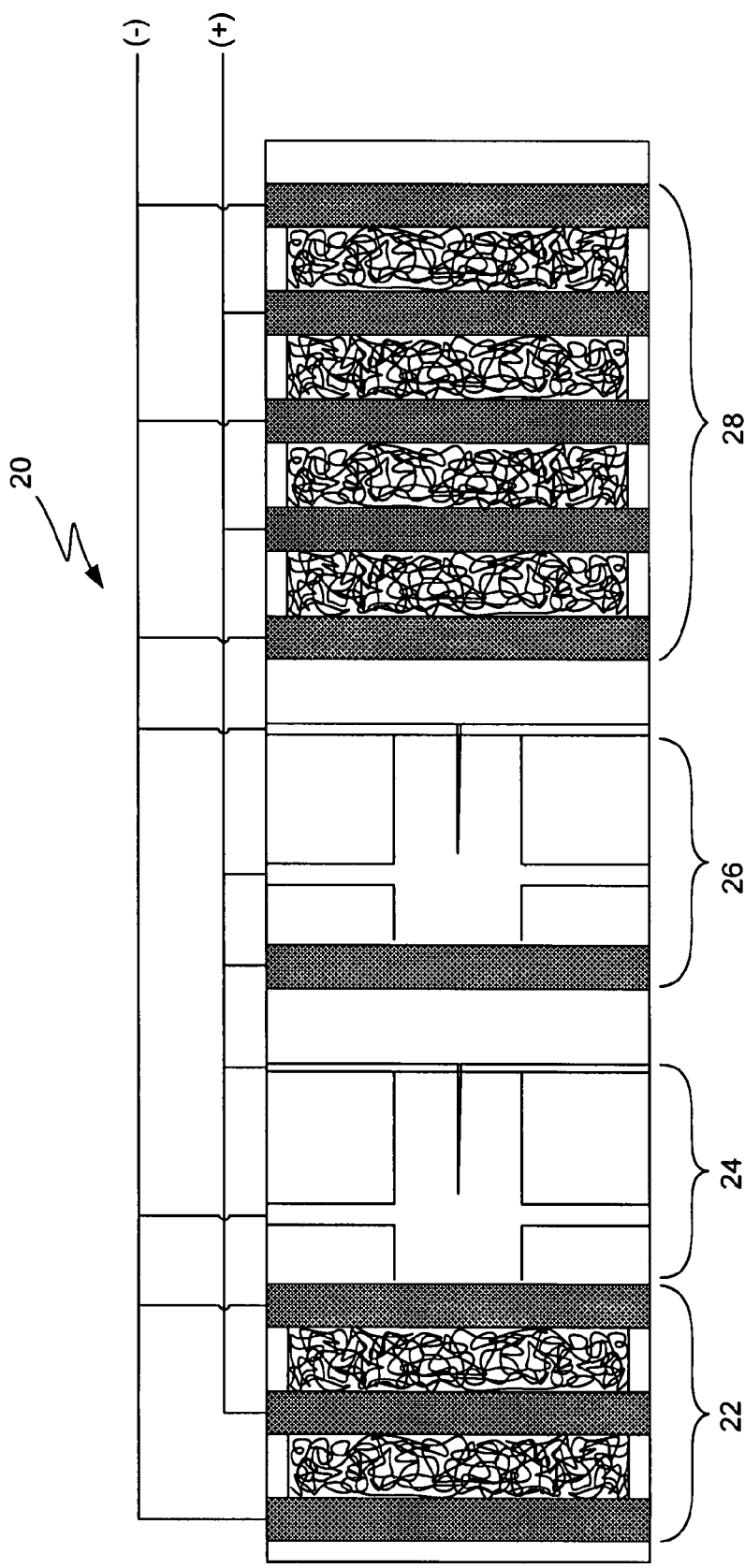
FIG. 1 diagrammatically illustrates an existing plasma based air purification and filtering system.

The present invention relates generally to fluid decontamination, filtering and/or purification devices. The plasma reactor described above and illustrated in FIG. 1 is different than traditional ion enhanced electrostatic filters in part because its ionizers (plasma generating chambers 26) provide significantly higher ionization levels than traditional ion enhanced electrostatic filters. By way of example, traditional ion enhanced electrostatic filters may utilize current densities on the order of 2 microAmperes/cm and generate a composite (average) electron density on the order of $10^{12}$ electrons/m$^3$. In contrast, the plasma generating chambers 26 described above may utilize current densities on the order of 3.5 microAmperes/cm and generate a composite electron density on the order of $10^{13}$ electrons/m$^3$, which improves the electron concentration (and thus the ion concentration) by about an order of magnitude. Such devices have been used commercially in Europe and Russia and have been observed to have significant advantages over traditional air purifying and/or filtering systems. Although the illustrated system works well, there have been continuing efforts to further improve the design.

It is noted that the ionizing chambers (e.g., the cylindrical or polygonal ionizing chambers 26, 140, 150) are frequently referred to as plasma generating chambers herein. This is because the plasma zone created around the ionizing electrode and the corresponding ion concentration within the chamber are generally substantially larger than those produced by the ionizers used in conventional ion enhanced electrostatic filters. As will be described in more detail, increasing the intensity of the ionization within the air purification and filtering device (reactor) can have a number of positive impacts on the efficacy and efficiency of the reactor.

The plasmas that are generated in the described plasma generators are commonly referred to as "non-thermal" or "cold" plasmas. That is, the plasma are generated at temperatures that are generally in the vicinity of ambient air temperatures in the environment that the devices are being used in and the electrons are at greatly elevated temperatures. This is as opposed to "thermal" or "hot" plasmas where both the ions and electrons coexist at elevated temperatures.

Figure 2:
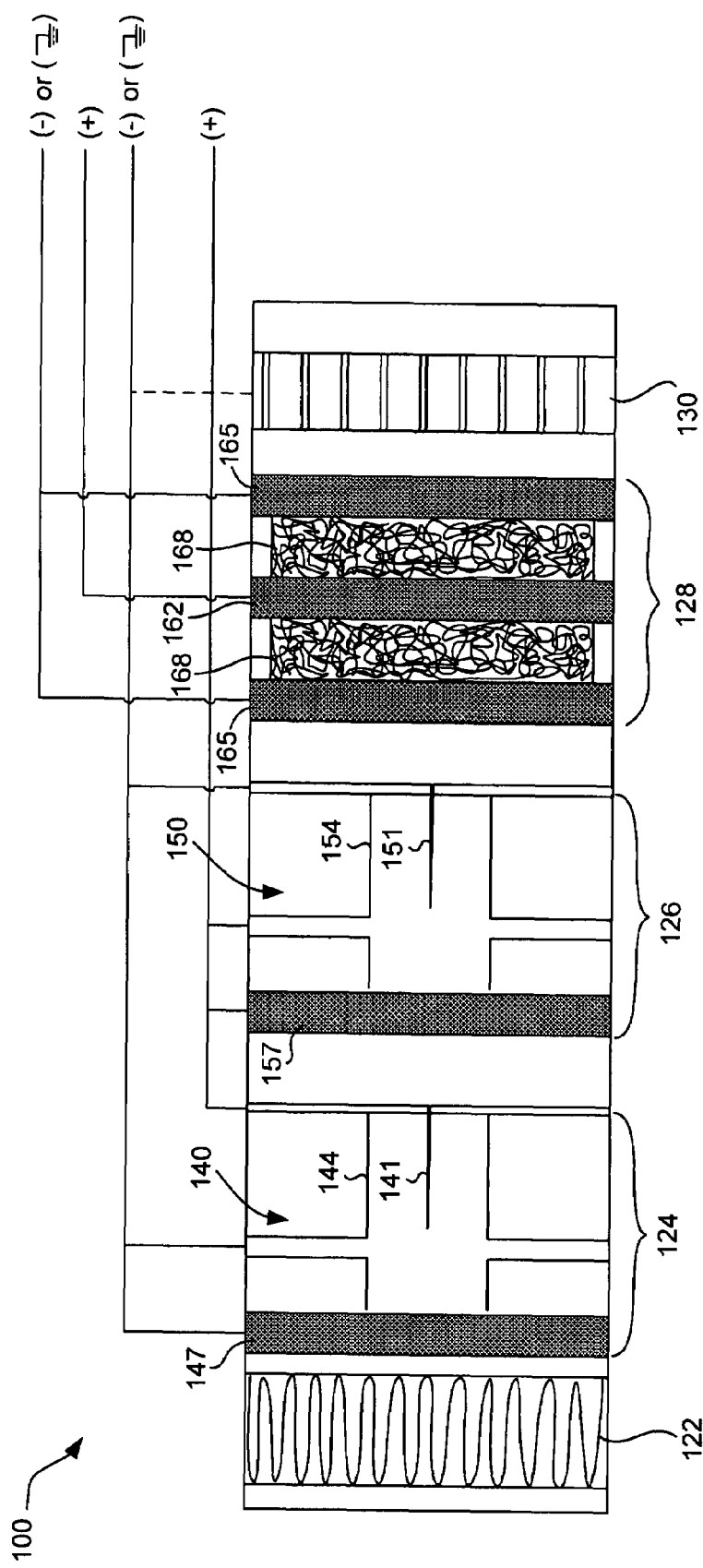
FIG. 2 diagrammatically illustrates a plasma based air purification and filtering system in accordance with an embodiment of the present invention.

Referring to FIG. 2, a plasma reactor in accordance with one embodiment of the present invention will be described. In this embodiment, the plasma reactor 100 includes a pre-filter 122, a positive plasma generator 124, a negative plasma generator 126, a series of active electrostatic filters 128 and a catalyst 130 that operates as a catalytic converter. These components are all arranged in series so that a gaseous fluid (e.g. air) enters the pre-filter 122 and sequentially passes through the plasma generators 124, 126, the electrostatic filter 128 and the catalyst 130.

The pre-filter 122 is generally intended to trap large particles. The pre-filter can be any type of filter including electrostatic filters and simple replaceable mechanical filters. In the illustrated embodiment, a simple replaceable mechanical non-woven mat type pre-filter is used. However, in other embodiments, active or passive electrostatic pre-filters may be used. One advantage to using an active electrostatic pre-filter is that it applies a dipole to particles entering the reactor thereby making them even more susceptible to the plasma chamber.

The Plasma Generators

Figure 3B:
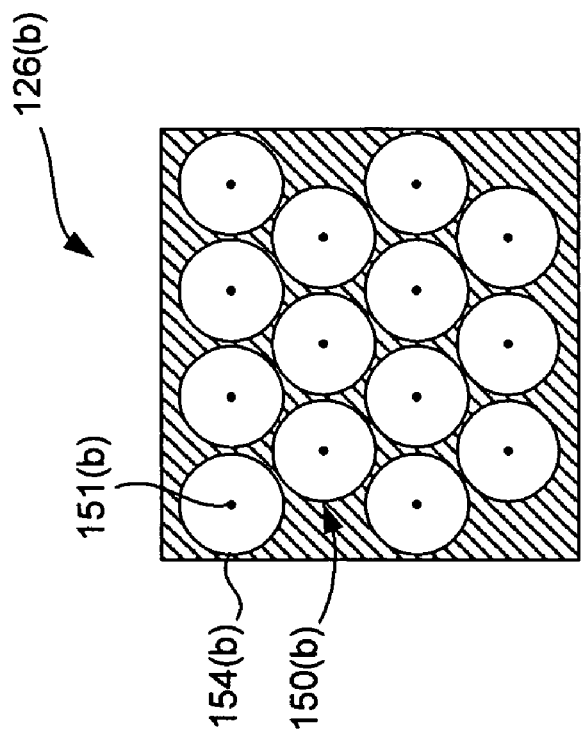
FIG. 3b is a diagrammatic end view of a plasma generator that is composed of a plurality of adjacent cylindrical plasma chambers arranged in parallel.
Figure 3A:
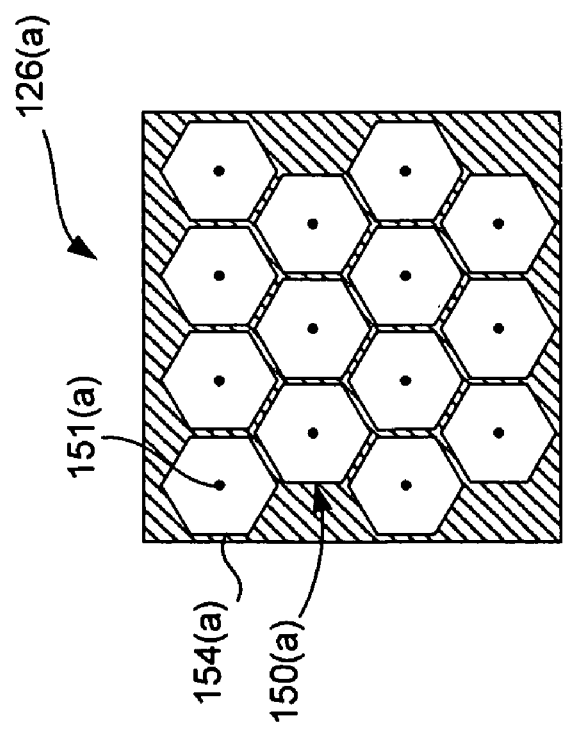
FIG. 3a is a diagrammatic end view of a plasma generator that is composed of a plurality of adjacent hexagonal plasma chambers arranged in parallel.

The positive plasma generator 124 is arranged to generate a positively charged cold plasma. In the embodiment shown, the plasma generator is composed of a plurality of adjacent plasma chambers that are arranged in parallel, as illustrated in FIGS. 3(a) and 3(b). Suitable plasma generator arrangements are described in the aforementioned '600 patent and co-pending U.S. application Ser. No. 10/450,565 filed Jun. 18, 2003 (now U.S. Pat. No. 7,198,660), which are incorporated herein by reference. Each chamber 140 includes a needle type positive discharge electrode 141, chamber walls 144 and a receptor electrode 147. The chamber walls 144 are also configured to operate as a receptor. When the pre-filter is an active electrostatic pre-filter, the receptor electrode 147 may optionally also be used as one of the electrodes in the pre-filter. In order to generate a cold plasma, a high potential difference is applied between the discharge electrode 141 and the receptor electrode 147. By way of example, voltage differentials on the order of 4,000 to 20,000 volts (or higher) work well in many applications. A suitable voltage differential can be created by applying a high positive D.C. potential to the positive discharge electrode 141 while a ground potential is applied to both the receptor electrode 147 and the chamber walls 144. In other embodiments, a positive D.C. potential may be applied to the positive discharge electrode 141 while a negative potential is applied to the receptor electrode and the chamber walls. Generally, it is the potential difference, rather than the absolute values of the respective potentials that is most important to the creation of the plasma.

The discharge (or corona) electrode 141 is preferably arranged substantially co-axially with the chamber walls 144, substantially in parallel to the direction of the net gas flow through the chamber. The cross sectional shape of the chambers may vary somewhat.

The negative plasma generator 126 is constructed similarly to the positive plasma generator 126, with the primary difference being that a negative potential (or ground) is applied to the negative discharge electrode 151 in each chamber 150, while a positive charge is applied to the receptor electrode 157 and the chamber walls 154. Of course, as is the case with the positive plasma generator 124, both electrodes could have the same polarity, so long as the potential difference between them is sufficient to generate the desired cold plasma. However, such embodiments are generally significantly less preferred.

In the diagrammatic illustration of FIG. 2, a single chamber is shown to represent the positive plasma generator and another single chamber is shown to represent the negative plasma generator. However, in most implementations it is desirable to provide a plurality of plasma chambers arranged in parallel for each plasma generator. The number of plasma chambers used for each plasma generator will depend on a number of factors including the size of the generators and the amount of airflow that the plasma reactor is designed to accommodate. By way of example, FIG. 3(a) diagrammatically illustrates a plasma generator composed of 12 adjacent plasma chambers arranged in parallel, with each plasma chamber 150(*a*) having a hexagonal cross section with co-axial needle type discharge electrode. FIG. 3(*b*) diagrammatically illustrates an alternative plasma generator composed of 12 adjacent plasma chambers 150(*b*) arranged in parallel, with each plasma chamber having a circular cross section with co-axial needle type discharge electrode. However, the cross sectional shape of the chambers may be any of a variety of other appropriate shapes (e.g., octagonal, or other polygonal shapes). These chambers are generally elongated in the direction of the airflow with the discharge electrodes extending substantially parallel to the airflow and generally co-axially with the chamber walls. These types of plasma chambers are generally referred to herein as co-axial plasma chambers.

In one particular implementation, the chamber walls 144, 154 are cylindrical and have an internal diameter in the range of 0.5 to 10 cm (as for example 5 cm). The discharge electrodes 141, 151 are positioned co-axially with the chambers. In another particular implementation, the chamber walls are hexagonal and have minimum chamber widths in the range of 0.5 to 10 cm (as for example 5 cm).

In the primary described embodiment, a pair of plasma generators (i.e., a positive plasma generator 124 and a negative plasma generator 126). However, in many applications only a single plasma generator would be desirable or necessary. The single plasma chamber could be either a positive plasma generator or a negative plasma generator.

Although, the described co-axial plasma chambers work very well and can be constructed at a relatively modest cost, it should be appreciated that a variety of other ion generating technologies may be used to create the desired plasmas or ionization zones. For example, RF, microwave, UV or other D.C. ion generators could be used in place of the co-axial plasma chambers in various embodiments. In other applications it will be desirable to combine different types of ion/plasma generators in the same reactor. For example, it may be desirable to combine a UV ion generator in combination with the described co-axial D.C. ion generators. These types of arrangements are believed to have particularly interesting applications in some of the catalyst-enhanced reactors described below.

One advantage of the described ion generators is that they only require the use of relatively simple D.C. power supplies, which today are generally significantly cheaper than corresponding A.C. power supplies. However, as the cost of power supplies at the required potentials decrease, this advantage may mitigate somewhat. The co-axial plasma chambers are also well suited for creating the non-thermal (cold) plasmas that are used in the described plasma reactors.

In the commercial implementation described above with respect to FIG. 1, one of the ionizing electrodes was grounded while a D.C. potential of either 4000 was applied to the opposing electrode. At these voltage levels, ozone is not generated in significant volumes and therefore, the reactor can be run for extended periods of time without an accompanying buildup of ozone in the room where the device is being used. The device also had a boost mode where a D.C. potential of 7600 volts was applied. In the boost mode, the amount of ozone generated was slightly less than 50 ppb. Many governments have rules or guidelines regarding the ozone concentration levels that humans may be safely exposed to. By way of example, the U.S. Occupational Safety and Health Administration (OSHA) has promulgated guidelines that mandate that humans should not be exposed to ozone concentrations above 50 parts per billion (ppb) for extended periods of time (e.g. 8 hours). Thus, operation of the reactor in the boost mode for and extended period of time could have the undesirable effect of injecting an undesirably high level of ozone into the room.

As will be described in more detail below, the embodiment illustrated in FIG. 2 includes a catalyst 130. The catalyst provides a number of potential benefits, one of which is that it can significantly reduce (or substantially eliminate) ozone from the purified air stream that leaves the reactor. Because of the ozone reduction, the described reactors can readily be run at higher potential differences between the discharge and receptors electrodes in the plasma chambers. By way of example, plasma generating chambers 124, 126 described above operating at a potential difference on the order of 8,300 volts may utilize current densities of 5 microAmperes/cm (or greater) and generate a composite electron density on the order of $10^{14}$ electrons/m$^3$. Such an electron concentration (and thus the ion concentration) is about an order of magnitude higher than the plasmas generated by the plasma generators described with reference to FIG. 1 and two orders of magnitude higher than more conventional ion enhanced electrostatic filters. Higher potential differences can even further increase the intensity of the plasma that is generated. The higher ionization levels within the reactor improve the efficiency and efficacy of the reactor in several respects.

Even with the ozone reduction, there are a number of other practical limits on the magnitude of the potential difference that can be utilized within the plasma chambers. Most notably arcing within the plasma chambers is highly undesirable and therefore the voltage differential cannot be increased so much that arcing begins to occur.

In one particular implementation, the chamber walls 144, 154 are cylindrical and have an internal diameter of 5 cm. The discharge electrodes 141, 151 are positioned co-axially with the chambers. In such a design, arcing may begin to occur within the plasma chambers if the potential difference between the electrodes is on the order of 13,000 to 20,000 volts. This limits the voltage differential that can be applied in such a chamber. However, since the geometry of the plasma chamber is particularly efficient, plasmas having high ion concentrations can readily be generated. Of course the breakdown (arcing) voltage for a particular reactor design may vary significantly with the size, geometry and design of the plasma chamber.

The Electrostatic Filters

The electrostatic filters 128 are located downstream of the plasma generators 124, 126. The electrostatic filters 128 are arranged in series and the number of electrostatic filters provided may be varied to meet the needs of a particular application. Typically, between one and five electrostatic filters are used. Each electrostatic filter 128 includes porous positive and negative electrodes 162, 165 that are separated by a suitable porous dielectric material 168. The electrodes 162, 165 are porous so that air passing through the reactor can pass through the electrodes. A relatively high potential difference is applied across the dielectric material. By way of example, potential differences of 4-40,000 volts or greater are preferred. Generally it is desired (but not required) to generate a field having a strength of at least 1000 V/cm. In some designs, the potential difference between the electrostatic filters electrodes is the same as the potential difference between the discharge and receptor electrodes in the plasma generators. However, this is not a requirement, and often it may be desirable to utilize higher potential differences for the filter electrodes. By way of example, such an arrangement is illustrated in the embodiment of FIG. 2.

The electrodes may be formed from a variety of different materials. By way of example, metals, conductive polymers or other conductive materials can be used to form the electrodes. In one specific embodiment, metallized open cell foams as described in U.S. Pat. No. 6,805,732 are used to form the electrodes. Other suitable electrodes are described below. The dielectric 168 can also be formed from a variety of different materials. One suitable dielectric material is described in the '732 patent.

Non-Woven Electrostatic Filter Dielectric

Figure 4:
FIG. 4 diagrammatically illustrates a high porosity, non-woven fabric mat that may be used to form the dielectric of an electrostatic filter in accordance with one embodiment of a first aspect of the invention.

An improved dielectric material for use in electrostatic filters will be described with reference to FIG. 4. The figure is a photo that illustrates a small segment of the dielectric. In this embodiment, a high porosity, non-woven fabric mat is used to form the dielectric. A variety of different dielectric materials can be used to form the mats. By way of example, polyester, polyurethane, polypropylene and other polymeric dielectric materials work well. Alternatively, other extrudable dielectrics including ceramics (e.g. silicon glass) could be used. Typically hydrophobic materials (such as polyester) are preferred, although particularly when insulated electrodes (as described below) are used, the hydrophobic characteristics of the dielectric become less important.

Preferably the dielectric mat has a high void fraction. That is, the vast majority of the mat is composed of pores as opposed to threads. By way of example, mats having a void fraction of at least 97% and more preferably more than 99% work well. Generally, the fibers should have a length to maximum thickness ratio of greater than 10 although substantially higher length to thickness ratios (e.g. ratios on the order of 100,000 or greater) would be typical for mats formed from small diameter polyester threads. The mats can be made using a variety of conventional non-woven matt fabrication processes. By way of example, conventional melt blowing and spin bond manufacturing techniques may be used to form appropriate mats from extruded threads. After formation, the mats can be cut to a desired size. One advantage of such an approach is that the resultant mats have pores that are statistically substantially equally sized and open in three dimensions. When the dielectric mats are placed into the electrostatic filter, they are preferably not significantly compressed. Therefore, when the filters are in use, the dielectric layers have a very high void fraction (e.g., preferably at least 97% and more preferably more than 99%). The high void fraction means that the filters impart relatively minimal drag to the airflow passing through the filter and they have a lot of space (i.e., the voids) for collecting particles.

As will be appreciated by those familiar with the art, the tortuosity of a mat is the ratio of the effective channel length to the thickness of the dielectric. The effective channel length is the distance a typical air particle will travel as is passes through the dielectric. The thickness is the straight line path through the mat in the direction of the air flow. It should be appreciated that the fluid passing through the dielectric will be diverted somewhat (and sometimes extensively) by the fibers. The mats preferably have a tortuosity of at least 1.2 which would require that the average (mean) air particle travel at least 20% further within the dielectric than it would if it followed a straight line through the dielectric. More preferably the tortuosity would be more than 1.7 (a 70% increase) or more that 2.0 (a 100% increase) and still more preferably at least 5 (a 400% increase). It should be appreciated that higher tortuosity causes more deflection of particles passing through the dielectric thus providing a higher probability that the particles will interact with mats fibers.

It has been determined that the field strength within the electrostatic filter is enhanced when the diameter of the threads 160 that form the mat are reduced. An enhanced field strength within the dielectric tends to increase the collection efficiency of the electrostatic filter. Accordingly, in order to enhance the strength of the field generated within the filter, it is desirable to utilize small diameter threads to form the dielectric. By way of example, threads having a cross sectional diameter of less than approximately 100 microns, as for example, threads having a cross sectional diameter in the range of approximately 0.1 to approximately 50 microns are preferred. In one specific embodiment, polyester threads having a diameter of 35 microns or less are used. Threads having a diameter of less than 10 microns work even better. It is believed that smaller diameter threads work better because their smaller transverse radius of curvature effectively makes sharper "points" which serve as focal points that enhance the electrostatic field.

It is believed that the radius of curvature of features in the dielectric material has a significant impact on the strength of the field created within the electrostatic filter 128. However, the effect is not necessarily dependant on the diameter of the thread as a whole. Rather, features along the perimeter of a thread that have a smaller local radius can be used to further improve the nature of the electrostatic field generated within the dielectric.

Most commercially available polymer threads have a substantially circular cross sectional shape. However, threads having alternative cross sectional geometries, which have smaller local radii along their perimeters, can be used to further improve the strength of the electrostatic field generated within the dielectric. Referring next to FIGS. 5(a) to 5(h) a variety of cross sectional shapes for the fiber threads that would be suitable to create the electrostatic filter are illustrated. Each of the threads illustrated in FIGS. 5(b) to 5(h) have cross sectional shapes that have multiple regions of small transversal radius of curvature along its perimeter.

Figure 5D:
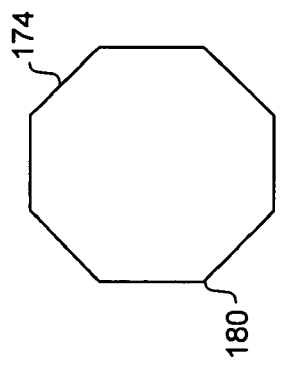
FIGS. 5(a)-5(h) diagrammatically illustrates cross sectional geometries of a few different fibers that are suitable for use as the dielectric in an electrostatic filter.
Figure 5C:
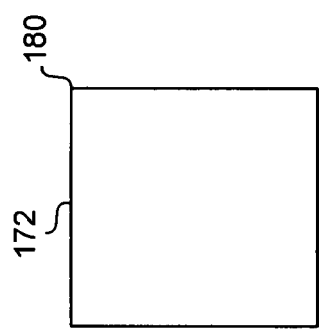
Figure 5B:
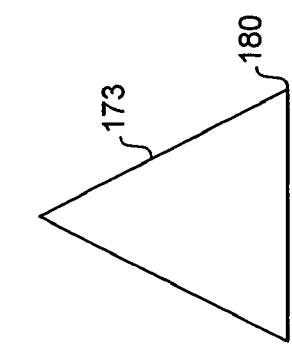
Figure 5A:
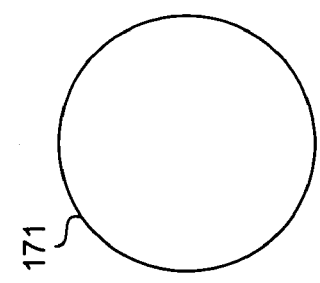
Figure 5H:
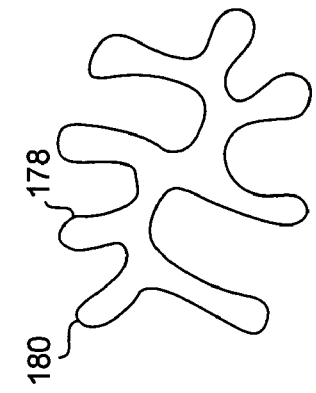
Figure 5G:
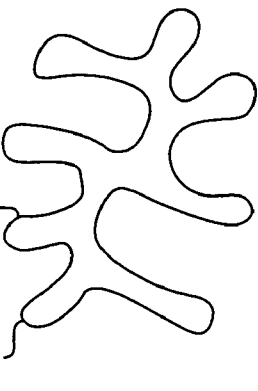
Figure 5F:
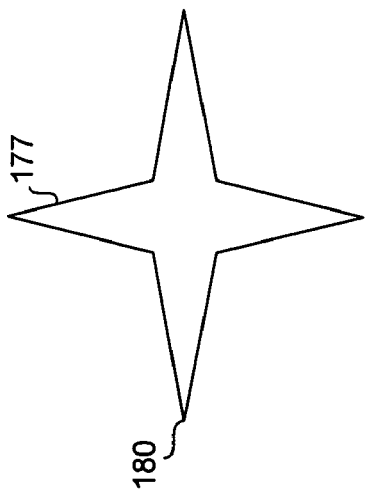
Figure 5E:
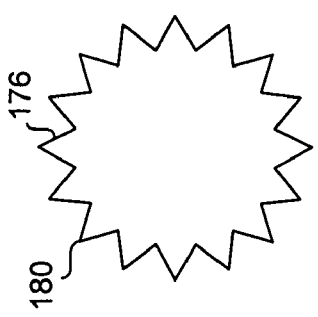

FIG. 5(a) illustrates a thread 171 having a circular cross sectional shape. The thread 172 in FIG. 5(b) has a rectangular (in this case substantially square) cross sectional shape. Each of the corners of the rectangular cross section constitutes a localized region 180 of small transversal radius of curvature along the perimeter of the thread. Thus, in this embodiment, there are four such regions 180 along the perimeter of the thread 172. The thread 173 in FIG. 5(c) has a triangular cross sectional shape. The thread 174 in FIG. 5(d) has a hexagonal cross sectional shape. FIG. 5(e) illustrates a thread 175 having an oval cross sectional shape. FIG. 5(f) illustrates a thread 176 having a star polygon shaped cross sectional profile. FIG. 5(g) illustrates a thread 177 having a star shaped cross section. FIG. 5(h) illustrates a thread 177 having a bulbous cross sectional shape. Each of these thread geometries have localized regions 180 having a small transversal radius of curvature along their perimeter. The radius of curvature of the localized regions 180 can be significantly smaller than the radius of curvature of even small diameter circular cross sectional threads. Accordingly, they work well to enhance the electrostatic field within the dielectric. In other respects, these threads can be used to create dielectric mats having similar void fractions, tortuosities, cross sectional thread widths (diameters) etc. similar to the circular cross section threads discussed above. Of course, a variety of other thread geometries that have small localized transverse radius of curvature can be used advantageously as well.

Insulated Electrostatic Filter Electrodes

When the plasma reactor 100 is in use, dust and other airborne particles collect within the filters 128. As the dust collects, it tends to cake on the dielectric, and to some extent on the electrodes themselves. As the amount of dust within the filter increases through extended use, the dust cake can build up sufficiently to form a continuous dust "path" between the electrodes. The dust is generally an electrical insulator. However, if the accumulated dust gets very moist, water carried by the dust can make the dust cake sufficiently conductive to cause arcing (shorting) between the electrodes. This problem is amplified in humid environments since the humidity in the air tends to moisturize the dust, thereby making the dust cake more conductive.

A variety of different approaches can be used to deal with the problem. One approach is to simply change or clean the electrostatic filter periodically. In most medical and residential applications, changing or cleaning the electrostatic filters on an annual basis is sufficient to prevent arcing. However, such an approach requires a periodic maintenance program.

The shorting problem has been observed in many active electrostatic filter applications and therefore attempts have been made to address the problem. One proposed approach contemplated insulating the electrodes. See, e.g., the 1983 Lawrence Livermore National Laboratory manuscript entitled "Electric Air Filtration: Theory, Laboratory Studies, Hardware Development, and Field Evaluations." Insulating the electrodes eliminates the shorting, however, charges having a polarity opposite to the polarity of the insulated electrode tend to accumulate on the surface of the insulation. That is, the insulation itself, or the dust layer on an insulated electrode tends to accumulate a charge that is opposite the polarity of the adjacent electrode. This opposite charge is attracted by the strong charge on the adjacent electrode. In practice, this buildup of charge is relatively slow and the actual amount of opposing charge that accumulates on the adjacent dust may be relatively small. However, it tends to drastically reduce the field within the dielectric 168 thereby significantly reducing the effectiveness of the electrostatic filter. In many systems, this type of degradation may occur over a period of several days.

U.S. Pat. No. 5,549,735 describes a system that attempts to address the problem by insulating only one of the two electrodes in an electrostatic filter. An ionizer is positioned adjacent the insulated electrode upstream of the filter. The ionizer precharges the air passing through the filter to the same polarity as the insulated electrode. Therefore, any charge that seeks to accumulate on the surface of the insulated electrode is quickly neutralized by charges from the ionized air passing thereby. Although this type of approach can work well in many applications, it leaves the second electrode uninsulated and it is not an ideal solution for devices having a series of electrostatic filters. Also, if a portion of the insulated electrode is blocked so that it is relatively far away from the ionized air stream, the ionized air may not adequately dissipate the opposing charge buildup in that region of the filter, which tends to reduce the filter's efficiency.

Figure 6:
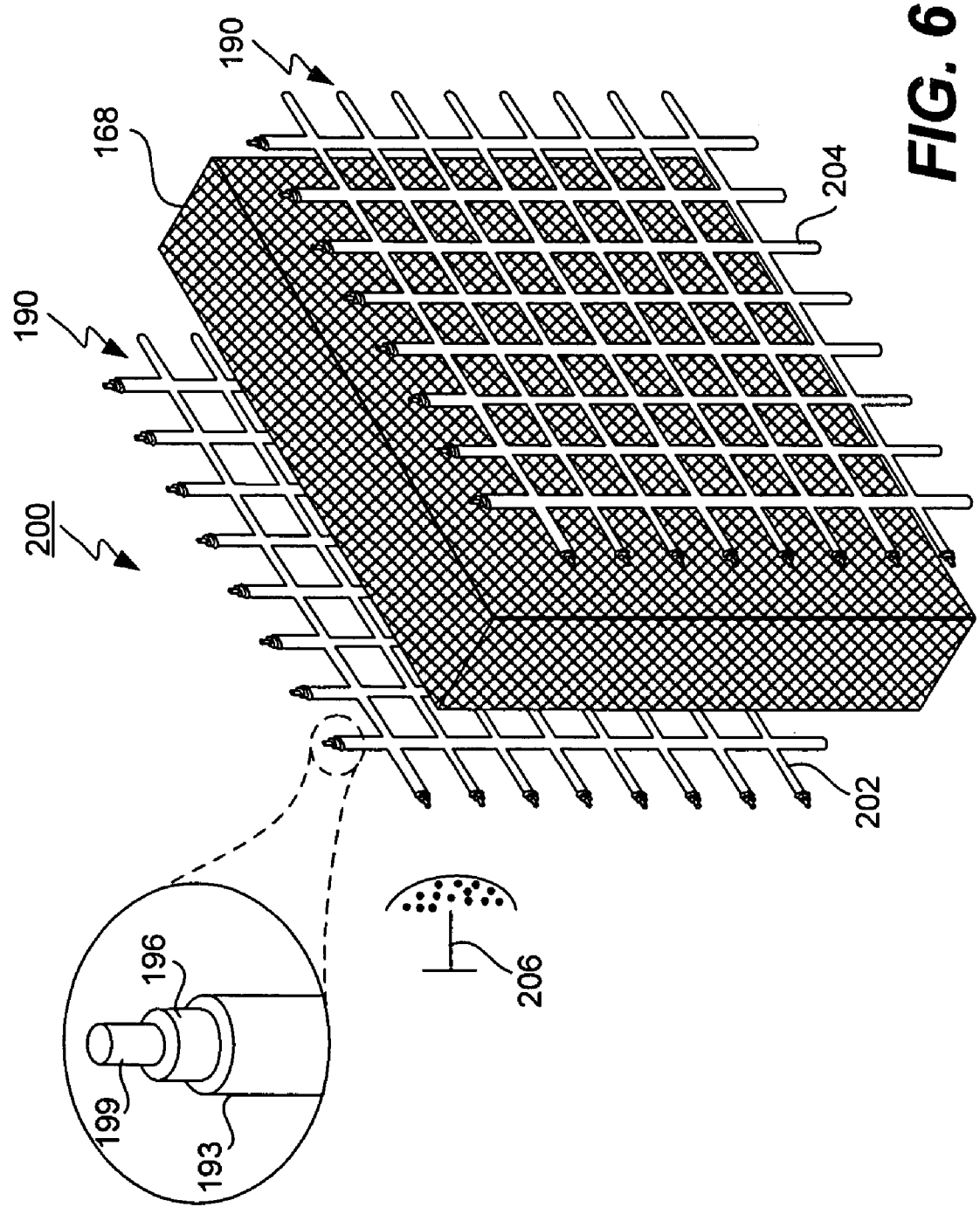
FIG. 6 is a diagrammatic illustration of a metallized insulated electrostatic filter electrode design suitable for use in accordance with an embodiment of another aspect of the present invention.
Figure 7B:
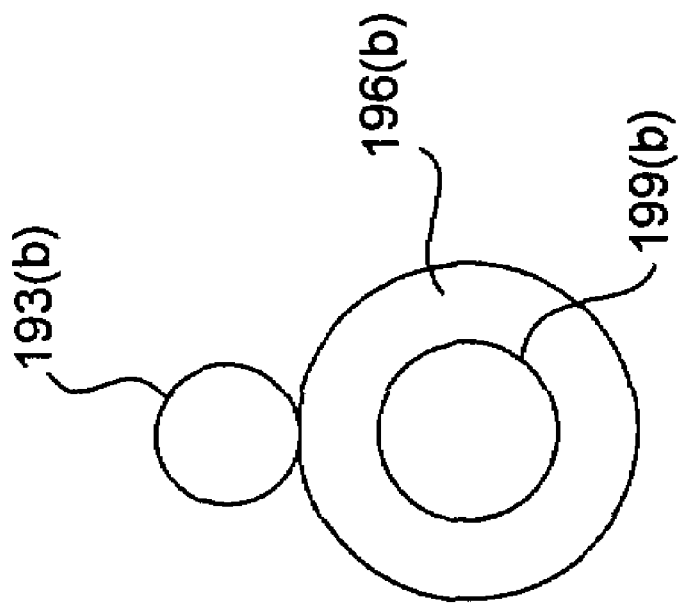
FIGS. 7(a) and 7(b) are cross sectional views of a couple of different metallized insulated electrode designs.
Figure 7A:
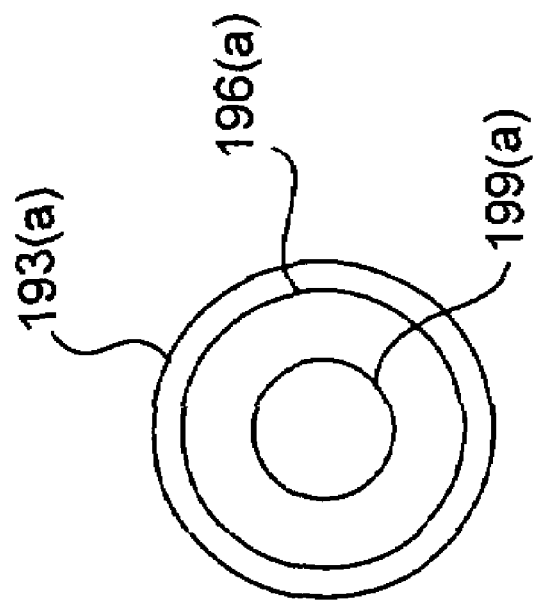

In the following description, a variety of arrangements (charge distribution grids) are described that can be used to distribute, mitigate or prevent the local accumulation of opposing charges on the surface of an insulated electrode. Referring next to FIG. 6, an electrode design in accordance with one embodiment of the present invention will be described. In the illustrated embodiment, a simple grid 190 is used as the electrode. However, in alternative embodiments, other porous electrode designs (such as the metallized open cell foam based electrodes described above) may be used. Both of the electrodes are electrically insulated. As best seen in FIG. 7, a metallization layer 193 is applied over the insulation 196, which covers the electrode 199. The metallization layer 193 acts as a charge distribution grid and can be formed in a wide variety of manners. For example, the metal layer may be deposited over the insulation or may be part of a metallized paint or other coating that is applied to the insulated electrode as illustrated in FIG. 7(a). Alternatively, the charge distribution grid may take the form of a separate metal grid that is placed adjacent and in contact with, adhered to or bound to the insulated electrode as illustrated in FIG. 7(b). With any of these arrangements, any opposing charge buildup on an insulated electrode tends to distribute throughout the metallic distribution gird thus preventing local charge buildup, for example in regions where the electrode may be blocked from a flow of neutralizing ions.

In order to neutralize such an opposing charge buildup, the charge distribution grid is exposed to a charge source having the same polarity as the electrode. There are a variety of mechanisms that may be used to apply the neutralizing charge to the charge distribution grid. In the embodiment illustrated in FIG. 6, an electrostatic filter 200 has an upstream electrode 202 and a downstream electrode 204 that sandwich a dielectric 168. Both of the electrodes 202, 204 are insulated and have an external metallization layer that serves as a charge distribution grid. When one of the electrodes in the filter is located adjacent to a similarly charged ion source, then the ion source may serve as the charge source for the electrode much as described in the '735 patent. Electrodes that are not located adjacent such an ion source can be connected to an alternative suitable charge source. In the illustrated embodiment, an ion source 206 having the same polarity as the upstream electrode 202 is positioned upstream of the first electrode. With this arrangement, the ion source serves as the charge source that neutralizes any opposing charges that accumulate on the insulated upstream electrode. By way of example, in a plasma reactor such as the reactor illustrated in FIG. 2, an ion source (i.e., the second plasma generator 126) is readily available at least to the upstream electrode on the first electrostatic filter. Therefore, the second plasma generator 126 can be used as the ion source for the upstream electrode for the first electrostatic filter.

If the entire surface of an insulated electrode is exposed well to the ion source, then the charge distribution grid could be eliminated since any opposing charges that are drawn towards the insulation would relatively quickly be neutralized by a passing ion. However, in many implementations it may not be practical to expose the entire surface of an electrode to the ion source. That is, there may be sections of the electrode that are not well exposed to the ion source. By way of example, if the ion source is a plasma generator having a plurality of cylindrical plasma chambers as illustrated in FIG. 3(b), then there may be certain dead spots on the filter that are not located directly behind a plasma generator cylinder. In such dead spots, opposing charges can accumulate on the insulation in localized regions even if other regions of the electrode are exposed to an ion source. Left alone on an insulated electrode, these charges would tend to decrease the field within the dielectric, thereby reducing the collection efficiency of the filter. However, the metallization layer substantially eliminates this problem. Specifically, in this case, the metallization layer also serves to distribute charges across the insulated electrode so that even opposing charges that would seek to accumulate in dead regions are neutralized.

In the embodiment illustrated in FIG. 6, the downstream electrode 204 is also insulated. The polarity of the downstream electrode is opposite to the polarity of the upstream electrode. Therefore, the ion source 206 does not operate to neutralize opposing charges that begin to accumulate on the downstream electrode (rather, if anything it would augment the charge buildup). Accordingly, another mechanism must be provided to neutralize charge buildup on the downstream electrode. If the downstream electrode is at ground potential, then the opposing charge buildup can be neutralized by simply grounding the metal layer on the downstream electrode. On the other hand, if the downstream electrode is charged positively or negatively, then another appropriate source such as charge pump 207 may be used to neutralize the undesirable opposing charges.

It should be appreciated that the voltage applied to the metallization layers does not need to be large and there is no need to try to match the voltage of the electrodes since the purpose of the metallization layers is not to generate a field within the dielectric. Rather, its purpose is primarily to mitigate or eliminate the buildup of parasitic opposing charges on the insulated electrodes. Indeed, if large potentials from significant current sources were constantly applied to the metal layers, an undesirable short could theoretically develop between the metal layers. Thus, in many applications it would be preferable to use relatively small charge/current sources.

The buildup of parasitic charges on the insulating layers tend to be quite slow. Therefore, in many applications it may be desirable to only periodically apply neutralizing charges to the metallization layers. The period between applications of the neutralizing charges to the metallization layers can vary significantly. By way of example, applying the neutralizing charges to the metallization at the frequency of only once an hour or once a day would likely be sufficient in most applications. Accordingly, the frequency at which the neutralizing charges are applied can be widely varied from periods of seconds, to minutes, to hours, or even days. When desired, the neutralizing charges can be applied to the positive and negative electrodes at different time to further reduce the risk of shorting. This allows relatively short high potential charges to be applied to the metallization layers. If a relatively high charge is applied to the metallization layer and retained under a capacitive effect, that charge tends to augment the field in the dielectric which can further increase the filter's efficiency, while it neutralizes any potential opposing charge buildup that would otherwise occur on the insulated electrode.

The described electrostatic filters can be used in a wide variety of electrostatic filter applications and are not in any way limited to use in the plasma reactors described above. Since the electrodes 202, 204 are both insulated, the filter is not susceptible to shorting between the electrodes or between an individual electrode and an adjacent component, even in the presence of a large buildup of very wet dust within the dielectric. The insulation also allows the (optional) use of higher potentials than might otherwise be desirable in certain applications.

The nature of the charge source used to drain opposing charges from specific insulated electrodes may be widely varied based on the nature of the application. When available, ion sources may be used as the charge source for any electrode. If both positive and negative ion sources are available, then both electrodes may be a neutralized by appropriate ion sources. When ion sources are not available, other structures, such as charge pumps may be used to apply the desired charge to the electrodes.

In still other systems, it might be expected that the charges that accumulate on the positive electrode may substantially balance the charges that accumulate on the negative electrode. In such a system, the opposing charges may be drained simply by electrically coupling the charge distribution grids together so that their accumulated charges effectively neutralize one another. Typically this would be done only on a periodic basis so that the connection between the charge distribution grids does not adversely affect the performance of the reactor. In situations where the electrostatic filter is used in a larger system (such as the plasma reactor illustrated in FIG. 2), parasitic charges from other locations in the system may be used to neutralize or drain the metallization layers.

Another way to mitigate the buildup of charges on the insulated electrodes would be to periodically reverse the polarity of the electrostatic filters (or potentially all of the components within a plasma reactor) when the electrostatic filters are used within a plasma reactor. This can readily be done simply by switching the potentials that are applied to the opposing electrodes. In this situation, any charges that had built up on the insulation before a polarity reversal would enhance the induced electrostatic field in the polarity reversed filter, at least until that charge buildup had been mitigated through migration in the opposite direction.

Figure 8:
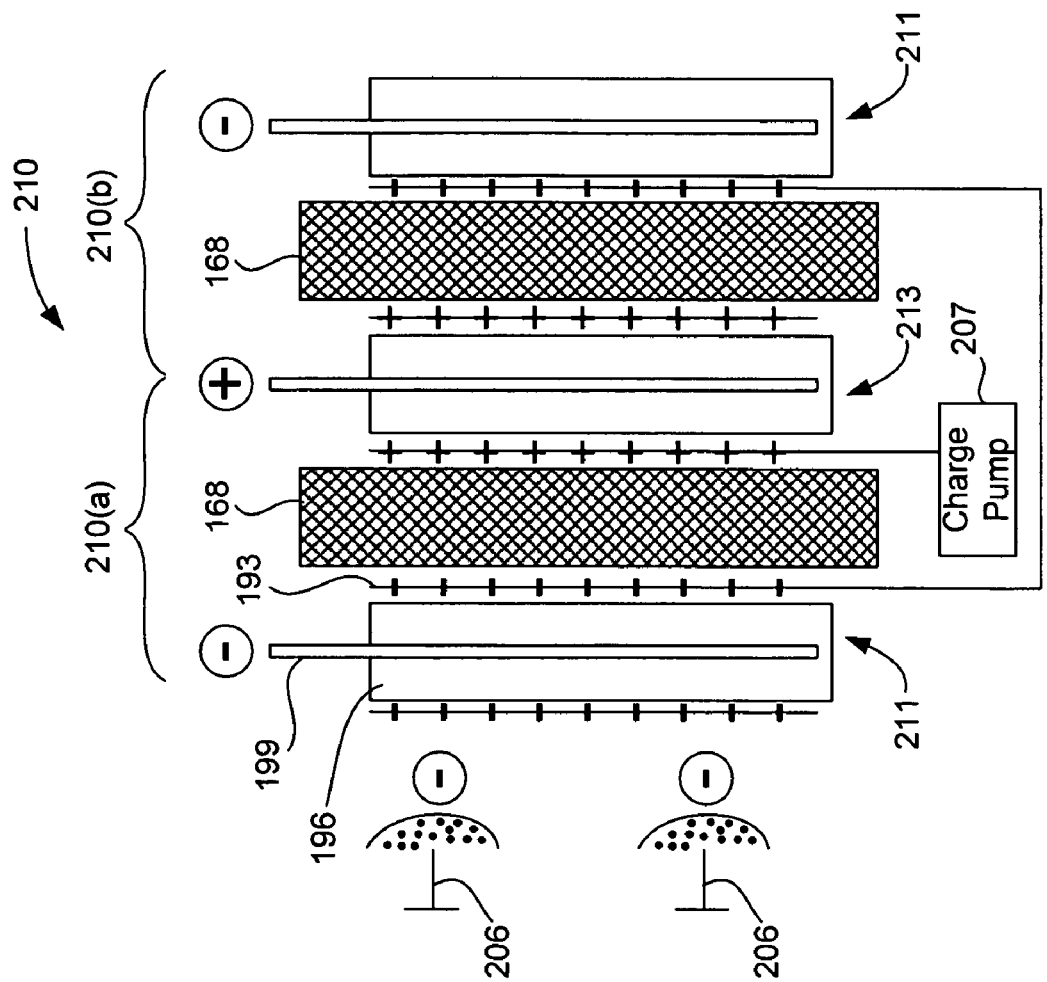
FIG. 8 is a diagrammatic illustration demonstrating one suitable arrangement for electrically connecting the metallization layers of a plurality of electrostatic filter electrodes.

Referring next to FIG. 8 another embodiment will be described. In this embodiment a series of three electrostatic filters is provided. Each electrostatic filter 210 includes metallized insulated positive and negative electrodes 211, 213, with the polarity of the electrostatic filters being alternated such that any particular intermediate electrode serves as an electrode for two adjacent electrostatic filters. The metallization layers for the negative electrodes are all electrically coupled and the metallization layers for the positive electrodes are all electrically coupled. The negative electrode in the first (i.e., upstream) electrostatic filter 210(a) is positioned adjacent a negative ion source which acts as the charge source for the metallization layer associated with the negative electrode in the first electrostatic filter. Since the metallization layers for the negative electrodes are all electrically connected, the ion source 215 adjacent the first electrostatic filter 210(a) acts as the charge source for the metallization layers associated with all of the negative electrodes. Similarly, the metallization layer associated with the positive electrodes are all electrically connected together and therefore, a single charge pump 217 (or other suitable charge source) may be used to feed all of the positive electrodes. Of course, charge pumps, ion sources or other suitable charge sources could be used for both the positive and negative electrodes or for any appropriate combination.

Promiscuous Insulation

There are a wide variety of insulation materials that are generally available and the insulating ability of such materials tend to depend in large part on the properties of materials, the thickness of the materials used, and the uniformity of the application of the insulation. Therefore, if a relatively poor insulator (sometimes referred to herein as a promiscuous insulation) is used on a high voltage electrode, some accumulated opposing charges will tend to migrate through the insulator to the electrode. If designed properly, this feature may be used to help reduce the buildup of opposing charges on the insulating layer. As indicated above, the buildup of opposing charge on the insulation layers is relatively slow. Therefore, if the thickness of an insulation material is chosen properly, then the insulator may "leak" enough charge to mitigate the buildup of opposing charges on the surface of an insulated electrode. At the same time, the thickness of the promiscuous insulation can be selected so that the insulation prevents shorting between the electrodes or between a particular electrode and an adjacent component. Such promiscuous insulation can be used together with or without the metallization layer described above. For example, in some embodiments, a high quality insulation with a metallization layer may be applied to one electrode, while a relatively promiscuous insulation may be applied to the other. In still other applications, both electrodes may be covered with promiscuous insulation. In some such embodiments, the metallization layer may still be provided on one or both of the insulated electrodes, while in others, the metallization layer may be eliminated. The promiscuous insulations may be used as the sole mechanism for draining opposing charges from one or both electrodes, or may be used in combination with other opposing charge neutralization mechanisms such as some of those described above.

The Catalyst

In specific commercial implementations of the plasma reactors described above with respect to FIG. 1, the plasma generators operated at a D.C. potential difference of 4000 volts, which could be boosted to 7600 volts for short time periods. As pointed out above, at a 4000 volts potential difference, the described device did not generate any significant amount of ozone. In the boost mode, some ozone is generated. Therefore if such a device is used in a closed space for a period of time in the boost mode, the ozone level within the room may built up to an undesirably high level because the half life of ozone in air is on the order of 20 minutes. As described above, one way to improve the performance of the reactor is to increase the intensity of the plasmas generated within the plasma generators. The intensity of ionization within a plasma can be increased by increasing the voltage differential used between the electrodes within the plasma generators. Increasing the ionization intensity significantly increases the levels of ozone (and other highly reactive gases such as nitric oxides ($NO_x$)) that are generated within the plasma reactor. This increased ionization helps improve the efficiency of the electrostatic filters 128 and helps improve the efficiency of the deactivation of biological agents that pass through the reactor. However, not all of the ozone and other reactive gases that can be generated within the plasma chambers may be consumed within the reactor.

There are a number of mechanism that can be used to reduce the concentration of reactive species in general and ozone levels in particular. In the reactor illustrated in FIG. 2, a perforated manganese dioxide ($MnO_2$) block 170 is used as a catalyst 130 that substantially eliminates ozone (and other reactive gases such as $NO_x$) from the air stream emerging from the reactor 100. There are a variety of manufactures of manganese dioxide catalyst blocks including Kocat, Inc of Korea, Nikki Universal of Tokyo, Japan, Nichias of Tokyo, Japan, Engelhard of New Jersey and Toyob from Osaka Japan.

Figure 9:
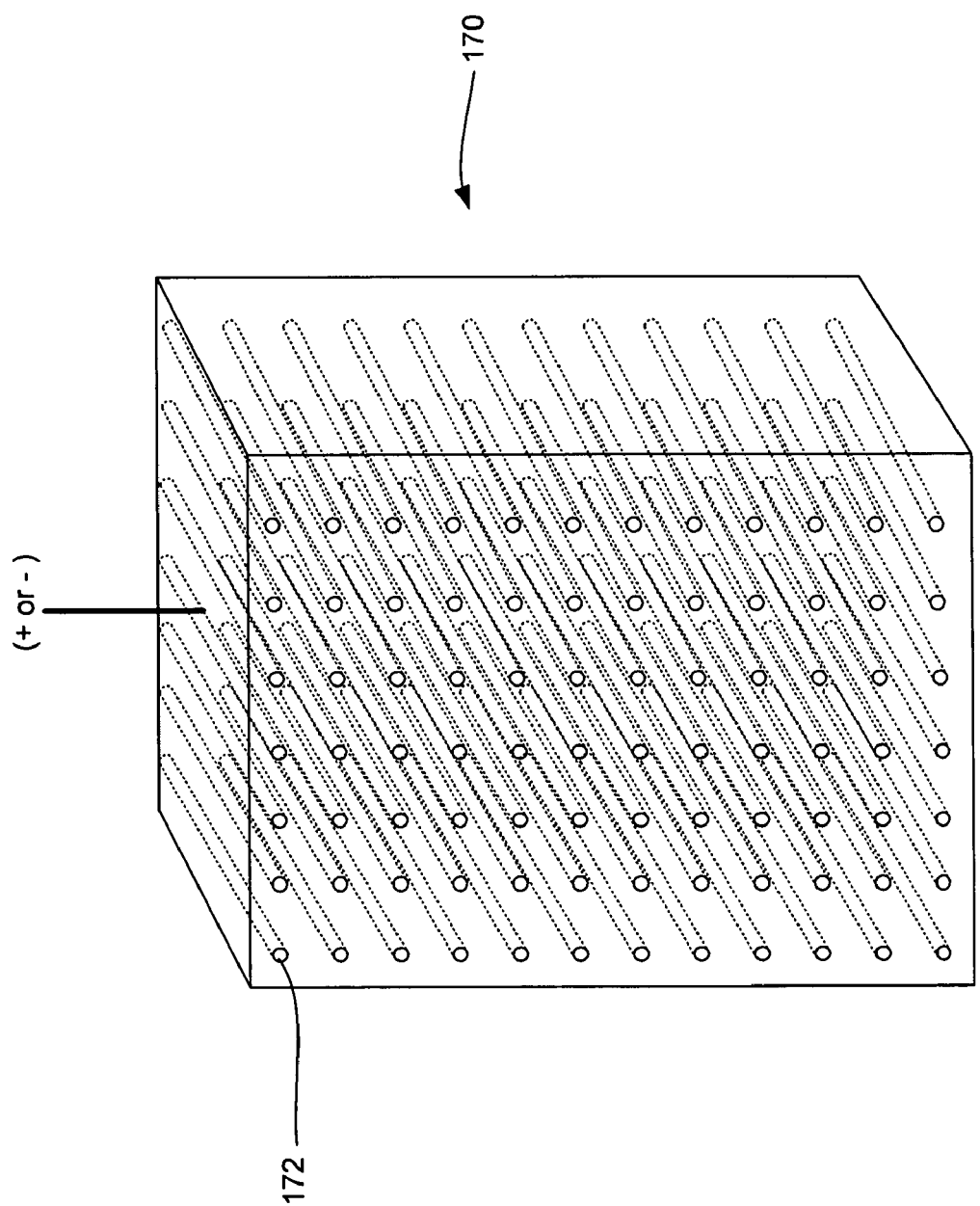
FIG. 9 is a diagrammatic illustration of a catalyst suitable for use in a plasma reactor in accordance with another aspect of the invention.

Referring next to FIG. 9, a suitable porous manganese oxide block 170 will be described. The block 170 is shaped to conform to the fluid flow channel within the reactor. Thus, in the illustrated embodiment, the block is generally rectangular. A large number of small diameter holes or passages 172 are formed in the block 170 so that the block does not impart a significant amount of aerodynamic drag to the air passing there through. In FIG. 9 the passages 172 are shown diagrammatically and it should be appreciated that far more passages would be provided than are shown. Additionally, there is no need for the passages to be straight. There are a variety of manufacturing techniques that may be used to produce the manganese dioxide blocks. In most cases powdered manganese dioxide is applied to a frame (such as a honeycomb support). The frame may be made of any suitable material including various metallic or ceramic materials.

The thickness of the block may be widely varied to meet the needs of a particular application. The effectiveness of the block will generally be a function of the amount of exposed surface area since, as will be appreciated by those familiar with the use of catalysts generally, the more surface area a catalyst has and/or the more exposure the catalyst has to the working fluid, the better it will generally perform. By way of example, block thicknesses on the order of 5 to 100 mm work well to eliminate ozone and other reactive gases. In one particular application, use of a high surface area 15 mm thick block works well to eliminate ozone from the purified air that leaves the reactor to a level that was not measurable (i.e., less than 1 part per billion (ppb)).

The use of the described catalyst allows the higher intensity plasmas to be used within the plasma generators. It should be appreciated that increasing the intensity of the plasma within the plasma chambers has a number of advantages. Initially, increasing the plasma concentration increases the efficiency of deactivation within the plasma chambers. Additionally, the enhanced ion concentration imparts a stronger charge to particles passing through the plasma generators, which makes the particles more likely to agglomerate, and more susceptible to being trapped by the electrostatic filters. Still further, increased ion concentration tends to result in increased ozone production, which results in increased ozone concentrations within the region of the electrostatic filters. The increased ozone level within the electrostatic filters improves the deactivation of biological entities caught by the filters.

The use of the catalyst also means that the reactor can actually reduce the amount of ambient ozone. This works because any ambient ozone in air that enters the reactor and remains free as it passes through the plasma chamber and electrostatic filters will be eliminated by the catalyst block 170. One environment where ambient ozone is a significant problem (in addition to biological deactivation) is in high altitude aircraft applications (such as airline, business jet, passenger jet, military and other such aircraft applications) because the ambient ozone level is significantly higher at the altitudes that are commonly used by modern aircraft. The described reactor can readily be sized for use in aircraft applications. In addition to purifying the air circulated within the aircraft, such a reactor can also be used to substantially eliminate ozone from outside air that is introduced into the cabin.

Ambient ozone and $NO_x$ are also significant components of smog, which can be harmful for patients with certain respiratory problems. Thus, the described reactors can be used to purify outside air in a variety of residential, commercial, and medical applications by substantially eliminating the reactive species from the air.

In addition to reactive species, there are a number of other contaminants that might be in ambient air. Generally, other air contaminants are grouped in three major categories. That is, particulates, biological contaminants and volatile organic components (which are generally gases). The electrostatic filters described above are generally very effective at removing particulates, including biological contaminants. The described reactor is also very effective at deactivating biological contaminants. There are several mechanisms within the reactor that are used to deactivate the biological contaminants. Initially, it is believed that at least some of the biological contaminants are deactivated within the plasma chambers. Biological contaminants that survive the plasma chambers are caught in the electrostatic filters located between the plasma generators 124, 126 and the catalyst 130. When the plasma generators are run at voltages that generate significant quantities of ozone, the region between the plasma generators 124, 126 and the catalyst 130 will be subjected to relatively high ozone concentrations. This high ozone region can be used advantageously to deactivate any biological entities that survive the plasma chambers. More specifically, any surviving biological entities (e.g., viruses, bacteria, spores, etc.) that are caught by the filters downstream of the plasma chambers will be deactivated over a relatively short time period by the relatively high ozone concentration level that is maintained in the region of the electrostatic filters. That is, such entities are deactivated under a "catch and burn" type scenario.

The use of a catalyst has several advantages over various ozone absorption technologies because the catalyst is not consumed as it eliminates reactive species from the air stream. In contrast, ozone absorber type products would typically be consumed somewhat during use, and therefore would generally require the absorber to be changed periodically.

As mentioned above, another class of contaminant found in many environments is volatile organic compounds (VOCs). Generally, electrostatic filters and enhanced electrostatic filters are not effective to remove volatile organic compounds because they are gases that will not be trapped by the filters. The plasma reactors illustrated in FIG. 1 may have some (relatively small) impact on volatile organic compounds due to the increased level of ionization within the plasma generating chambers 26, however they do not effectively remove most VOCs. Another property of magnesium dioxide is that it also acts as a catalyst for eliminating VOCs. However, magnesium dioxide tends to be more efficient at reducing ozone and $NO_x$ than it is at reducing VOCs. As discussed above with respect to ozone and $NO_x$, the effectiveness of the catalyst block 130 will generally be a function of the surface area that is exposed to the air stream. However, as will be described below, several enhancements have been made to improve the efficiency of the catalyst 130.

It should be appreciated that the by the time an air stream passing through the reactor enters the catalyst block 130 will typically have very few particulates (since it has passed through the electrostatic filters) but it will typically have a number of charged ions. In another aspect of the invention, in order to further improve the efficiency of the catalyst, the catalyst may be subjected to an electrostatic field and/or be turned into an electrode. Such a catalyst electrode tends to draw charged entities (e.g., ozone, $NO_x$ and certain charged VOCs) towards the catalyst material, which increases the probability that the charged entities will come into contact with the catalyst material so that they can be reduced, thereby increasing the efficiency of the catalyst.

In the embodiment illustrated in FIG. 2, the catalyst block 130 is not electrically charged. However, in an alternative embodiment (shown in dashed lines in FIG. 2), the catalyst block 130 may be turned into an electrode. Although magnesium dioxide itself is a dielectric material, the catalyst block 130 can readily be formed as electrode by using a metal (or other conductive) material as the frame for the catalyst and then electrically connecting the frame to an appropriate electrical source. As described above, magnesium dioxide catalysts are typically made by applying powdered manganese dioxide to support frames. Metal is often used as the frame material today so an appropriate electrode can easily be made by simply using a metal frame and providing access terminals on the metal frame. Of course, the catalyst electrode may be formed by a wide variety of other processes as well. A wide variety of metals may be used as the frame. By way of example, Aluminum works well.

The catalyst 130 is electrically connected in the reactor 100 to form an electrode. The catalyst may be used as a positive electrode, a negative electrode, or a ground electrode. In the embodiment illustrated in FIG. 2, the catalyst 130 is the last exposed element in the reactor. Therefore, for potential safety issues, if that catalyst is used as an electrode, it may be grounded so that it becomes a ground electrode. However, in other embodiments, the catalyst electrode 130 may be positively or negatively charged.

The catalyst electrode tends to draw charged entities (e.g., ozone, $NO_x$ and certain charged VOCs) towards the catalyst material, which increases the probability that the charged entities will come into contact with the catalyst material so that they can be reduced, thereby increasing the efficiency of the catalyst. This lateral movement of the charged entities also tends to promote mixing (and in some cases possibly even turbulence) within the channels 172, which again, improves the probability that entities that may not be charged (such as neutral volatile organic compounds like benzene, toluene, hexane, ethanol, etc. . . . ) will come into contact with the catalyst surface thereby again increasing the efficacy of the catalyst. In these embodiments, the catalyst electrode draws particles and gas-phase molecules to its surface via electrostatic forces. These forces can be columbic if the molecules/particles are charged or dipolar if the molecules/particles are neutral.

The effectiveness of the catalyst electrode is enhanced when it is used in conjunction with an electrode having the opposite polarity in order to effectively form a catalytic electrical sandwich. This can readily be accomplished by adding another (opposing polarity) electrode that cooperates with the catalyst electrode. Alternatively, the catalyst electrode can be used as one of the electrodes (preferably the last electrode) in the electrostatic filter block. When the catalyst electrode is integrated with an electrode of opposing polarity, the electrostatic forces that draw charged gas phase molecules towards the catalyst surface are significantly stronger.

As mentioned above, one common way of fabricating catalyst blocks is to apply powdered manganese dioxide to a honeycomb type frame. The effectiveness of the catalyst as an electrode can be increased by selecting a metal (e.g., aluminum) frame that has a number of sharp points in it. The advantage of the use of sharp points in an electrode is described in some detail in the above referenced U.S. Pat. No. 6,805,732 which is incorporated herein by reference. Thus, in one particular arrangement, the catalyst block may be formed on a metal honeycomb frame having, sharp points distributed (preferably relatively evenly distributed) throughout the frame.

Figure 10:
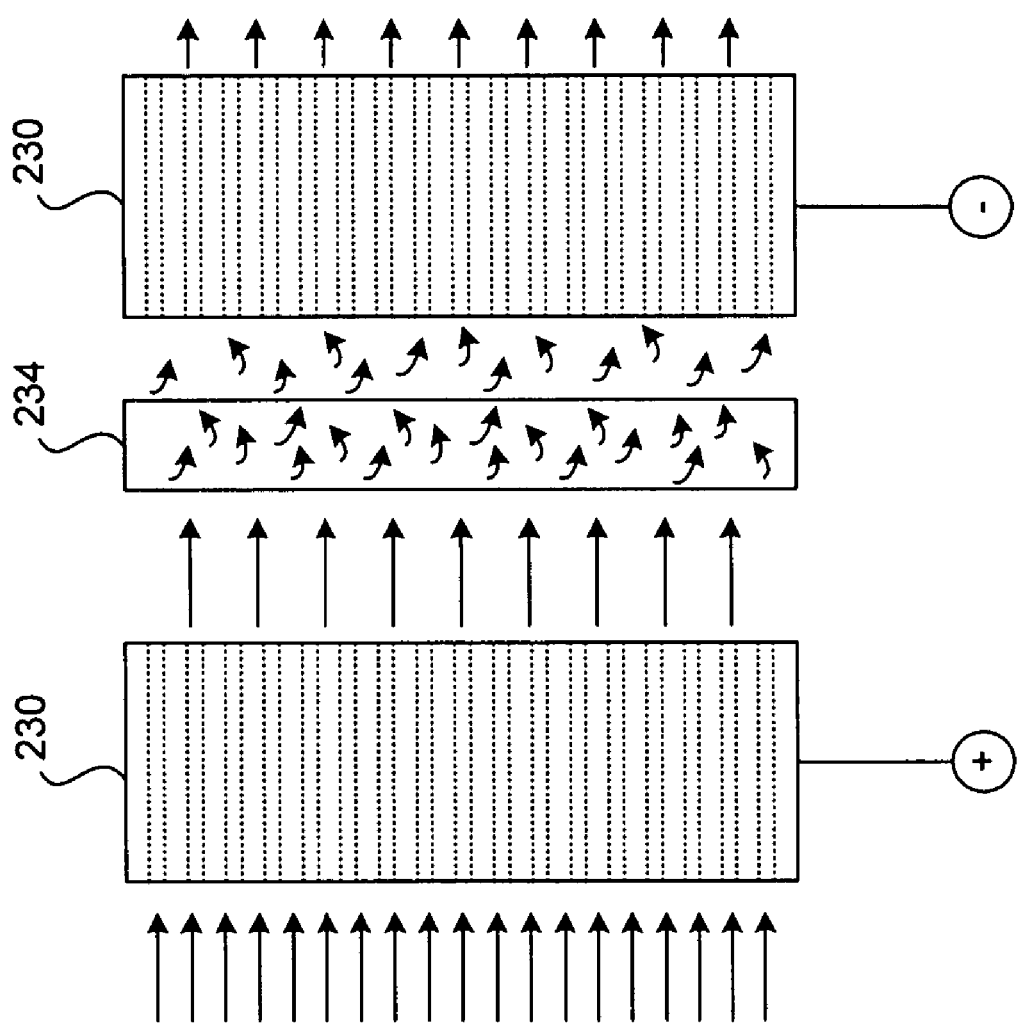
FIG. 10 is a diagrammatic illustration of an alternative catalyst arrangement.

Referring next to FIG. 10, another embodiment of the catalyst will be described. In this embodiment, a pair of catalyst blocks 230 are separated in space from each other. In the illustrated embodiment a mixing plate 234 is positioned between the catalyst blocks. The mixing plate 234 is designed to impart lateral movement to the fluid flow to again increase the probability that VOCs and reactive species within the air stream will come into contact with the catalyst walls. Even if the mixing plate is eliminated, providing a gap between the catalysts blocks 230 will promote some mixing (albeit less than is provided by the mixing plate). By way of example gaps on the order of between 0.5 to 5 cm work well and would be typical, although other spacings may be used as well.

Of course, more than two catalyst blocks can be provided and appropriate gaps, mixing plates or other structures can be introduced before or between the catalyst in order to promote better interaction between the air stream and the catalyst. The better interaction, in turn, tends in increase the efficacy of the catalyst. Some or all of the catalyst blocks may optionally be used as electrodes to even further promote the air/catalyst interaction. When two (or more) electrodes blocks are used, the polarity of the blocks may be alternated in order to further improve the efficiency of the catalyst.

Oxidation Catalysts

Figure 11:
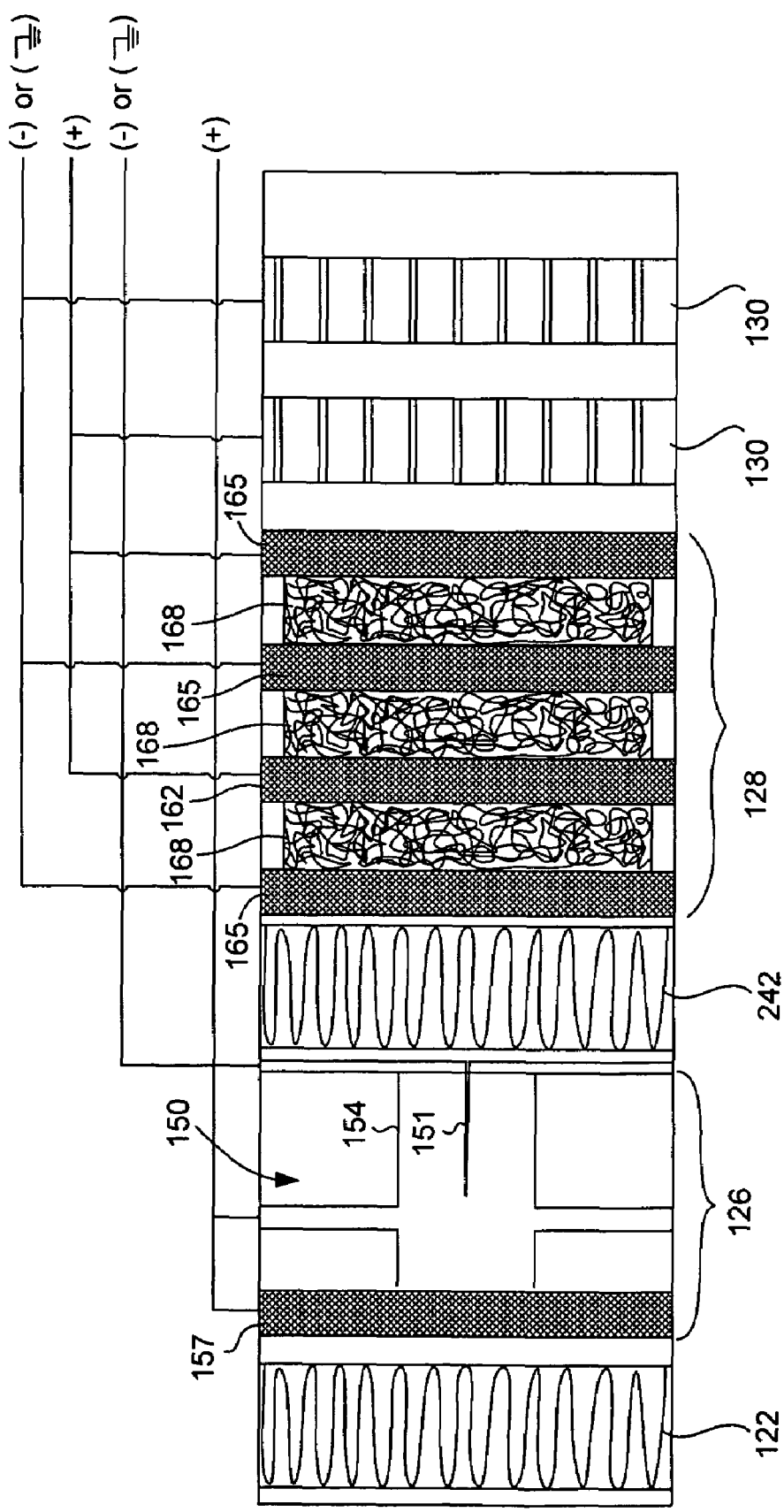
FIG. 11 is a diagrammatic representation of another reactor design that includes an oxidation catalyst.

Referring next to FIG. 11 another reactor design will be described. This reactor design is quite similar to the design of the reactor illustrated in FIG. 2, except that an oxidation catalyst 242 is added upstream of at least some of the electrostatic filters. Additionally, the number of various components provided are changed somewhat in an effort to illustrate some of the flexibility of the described system. In the illustrated embodiment, the oxidation catalyst 242 is positioned downstream of the plasma generator between the plasma generator 126 and the electrostatic filter 128. However, it should be appreciated that the oxidation catalyst can be provided at a variety of alternative locations within the reactor, although when it is susceptible to producing ozone as a byproduct, it should be placed upstream of the reducing catalyst 130.

There are a handful of known oxidation catalysts. By way of example, Barium Titanium Oxide ($BaTiO_3$), and Titanium oxide ($TiO_2$) work well at low (i.e. normal ambient) temperatures. Such catalysts are preferably located downstream of at least one of the plasma generators because the catalysts generally produce more oxidation species (e.g. ozone) in environments having higher ion concentrations.

The oxidation catalysts increase the ozone concentration level within the electrostatic filter, which further improves the deactivation efficacy of any biological entities that are trapped within the electrostatic filter. The oxidation catalysts are practical primarily because the reducing catalyst 130 is so effective at eliminating surplus oxidative species (e.g. ozone) from the fluid stream after is passes through the electrostatic filters. In addition to producing ozone, the oxidation catalyst 242 also oxidizes various volatile organic compounds (VOCs) and therefore can be quite helpful in reducing the VOCs concentrations within the fluid stream.

In the embodiment illustrated in FIG. 11, a pair of spaced apart reducing catalyst electrodes 170 are provided in place of a single reducing catalyst 130. The catalyst electrodes are subjected to charges of opposite polarity, thereby forming an electrostatic catalytic sandwich, which further improves the efficiency of the catalysts as described above. The embodiment illustrated in FIG. 11 also includes just one plasma generator (in this case negative plasma generator 126—although of course any other suitable plasma generator could be used). It also includes a series of three electrostatic filters.

As pointed out above, both the oxidizing and the reducing catalysts also have the benefit of destroying volatile organic compounds. However, their efficiency as eliminating VOCs is not as great as their ability to generate or eliminate oxidative species. In the various catalyst embodiments described above the systems are designed in large part to control the amount of reactive species within the reactor and/or the effluent stream. However, in some applications, VOCs may be of greater concern and therefore it may be desirable to design the reactor in a manner that is better arranged to destroy VOCs. This may be accomplished in a variety of manners. Virtually any of the components of the reactor may be coated with a catalyst in order to further improve the reactors VOC elimination efficiency. Specifically, various components of the electrostatic filters and the plasma generators may be coated with catalysts to improve the reactor's efficiency. For example, within the plasma generators, the chamber walls 144 and/or the receptor electrodes 147 may be coated with a catalyst such as manganese dioxide ($MnO_2$), Barium Titanium Oxide ($BaTiO_3$), and Titanium oxide ($TiO_2$). Similarly, such catalysts may be used as the insulator for the electrodes in the electrostatic filters or may coat the dielectric used in the electrostatic filters. For the most part, each of these applications will enhance the VOC elimination efficiency of the reactor. It should be appreciated that the use of manganese dioxide within the plasma chamber may reduce the ozone level within the generator and downstream of the generator. For a fixed potential difference between the discharge electrode and the receptor electrode, this may reduce the amount of ozone that is available to "catch and burn" biological entities within the downstream electrostatic filters. However, this is often not a problem because the reactor can be run at potential differences that would insure an excess supply of ozone and the prolonged ozone exposures applied to biological entities trapped within the electrostatic filter will be sufficient to deactivate the biological entities. Additionally, in some situations the use of a catalyst chamber wall coating may permit the plasma chamber to be operated at higher potential difference, which further increases the ionization level within the chamber and hence increases the efficiency of the overall reactor.

Applications

The described reactors may be used to decontaminate, purify and/or filter air (or other gaseous fluids) in a very wide variety of applications. By way of example, one application is in air purification and decontamination systems for hospital and/or other health care environments. In hospital environments nosocomial (i.e., hospital acquired) infections are well understood as a significant problem. Most notably, immune deficient patients can be very susceptible to infection and a significant percentage of complications and hospital related deaths are due to nosocomial infections. Therefore, one desirable feature for air purification systems intended for use in heath care environments is the complete deactivation of airborne biological agents that pass through the filters. The described reactors are well suited for such deactivation.

Another application described above is in aircraft filtering systems. In such applications, biological decontamination, filtering, ozone removal and VOCs removal are all desirable features and again, the described reactors are well suited for use in such applications. Another application is the filtering of air in commercial and residential building applications. In some environments, filtering and/or the removal of VOCs are considered particularly important. In others, biological decontamination is most important. In still other applications it may also be desirable to remove reactive species (e.g. ozone and NOx) from the environment.

In many applications, a desirable feature is the removal of a very high percentage of the airborne particles from the air passing through the filters. One widely used standard is referred to as a HEPA (High Efficiency Particle Air Filtration) filter. By definition, a HEPA filter must be able to remove at least 99.97% of the 0.3-micron airborne particles that pass through the filter. The described reactor can readily be designed to attain HEPA filter efficiencies.

Another large application is in the residential and commercial air handling markets where often it may be desirable to filter, decontaminate and/or purify air. In some applications the reactors may be incorporated into the heating ventilation and/or air conditioning (HVAC) systems within the buildings while in other situations they may be incorporated into devices intended to operate in local room or workspace areas.

It should be that the components of a reactor (e.g., the number, size and type of the ion or plasma generators, the number and type of electrostatic filters, the catalysts used—if any—) can be selected to meet the needs of a particular application.

Although only a few embodiments of the invention have been described in detail, it should be appreciated that the invention may be implemented in many other forms without departing from the spirit or scope of the invention. The inventions have been described primarily in conjunction with their integration into a plasma reactor based air decontamination, filtering and purification system. However, it should be appreciated that the majority of the inventions described herein can be used in a wide variety of other applications as well. For example, the electrostatic filter related inventions, may be used in any electrostatic filter application and they are not in any way limited to use in plasma reactors based decontamination and/or purification systems. Similarly, many of the catalyst related inventions can be used in a variety of different ion enhanced filtering applications. Thus, it should be apparent that the various described inventions can be used together or separately and they may be integrated as part of a plasma reactor or used in other filtering systems.

In the foregoing descriptions, the plasma generators and the various electrodes have been described as having potentials applied thereto. In some cases the applied potential is a ground potential. In other cases the applied potential may be a positive potential or a negative potential. In the description of the insulated electrodes, charge sources were applied to a charge distribution grid in certain embodiments. It should be apparent that at times, the charge source could simply be a ground as opposed to a source of positive or negative charges. Therefore, the present embodiments are to be considered as illustrative and not restrictive and the invention is not to be limited to the details given herein, but may be modified within the scope and equivalents of the appended claims.

What is claimed is:

1. An electrostatic filter suitable for collecting aerosol particulates carried in a fluid stream passing through the electrostatic filter, the electrostatic filter comprising:
   a first porous electrode formed from a conductive material having a porosity of at least 90%;
   a dielectric mat formed from a high porosity non-woven fiber having pores that have a void fraction of at least 97%, wherein the fibers have a maximum cross sectional thickness that is less than 100 microns and a length to maximum thickness ratio of greater than 10, and wherein the dielectric mat has a tortuosity of at least 1.7; and
   a second porous electrode formed from a conductive material having a porosity of at least 90%, the first and second porous electrodes being arranged to sandwich the dielectric mat, and arranged such that in operation a fluid stream to be filtered passes through the electrodes and the dielectric mat and the first and second porous electrodes may have a sufficiently high potential difference applied thereto to facilitate the creation of an induced electrostatic field within the dielectric mat, whereby the fluid stream passing through the dielectric mat would be subjected to electrostatic forces that are substantial enough to cause at least some of the particulates within the stream to adhere to the fibers of the dielectric mat.

2. An electrostatic filter as recited in claim 1, wherein the void fraction of the dielectric mat is greater than 99 percent.

3. An electrostatic filter as recited in claim 1 wherein the pores are statistically substantially equally sized and open in three dimensions.

4. An electrostatic filter as recited in claim 1 wherein the dielectric mat has a tortuosity of at least 2.

5. An electrostatic filter as recited in claim 1 wherein the maximum cross sectional thickness of the fibers is in the range 0.1 to 50 microns.

6. An electrostatic filter as recited in claim 1 wherein the fibers that form the dielectric mat are formed from a material selected from the group consisting of polyester and polypropylene.

7. An electrostatic filter as recited in claim 1 wherein a cross section of the fibers has at least one region of small transversal radius of curvature along its perimeter.

8. An electrostatic filter as recited in claim 1 wherein a cross section of the fibers has a plurality of distinct regions of small transversal radius of curvature along its perimeter.

9. An electrostatic filter as recited in claim 8 wherein the cross section of the fibers has a substantially polygonal shape.

10. An electrostatic filter as recited in claim 1 wherein at least one of the electrodes is formed from a metallized open cell foam structure.

11. An electrostatic filter as recited in claim 1 wherein the maximum cross sectional thickness of the fibers is less than 35 microns.

12. An electrostatic filter as recited in claim 1 wherein the maximum cross sectional thickness of the fibers is less than 10 microns.

13. An electrostatic filter as recited in claim 1 wherein at least one of the electrodes is insulated.

14. An electrostatic filter as recited in claim 13 wherein the insulated electrode has a conductive material disposed over at least a portion of the insulation that faces the dielectric.

15. An electrostatic filter as recited in claim 1 wherein the dielectric mat has a tortuosity of at least 5.

16. An electrostatic filter suitable for collecting aerosol particulates carried in a fluid stream passing through the electrostatic filter, the electrostatic filter comprising:
   a first substantially flat porous electrode formed from a conductive material having a porosity of at least 90%;
   a substantially flat dielectric mat formed from a high porosity non-woven fiber formed from a material selected from the group consisting of polyester and polypropylene, the dielectric mat having pores that are statistically substantially equally sized, are open in three dimensions, and have a void fraction of at least 99%, wherein the fibers have a maximum cross sectional thickness that is less than about 35 microns and a length to maximum thickness ratio of greater than 10 and wherein the dielectric mat has a tortuosity of at least 5; and a second substantially flat porous electrode formed from a conductive material having a porosity of at least 90%, the first and second porous electrodes being arranged to sandwich the dielectric mat, and arranged such that in operation a fluid stream to be filtered passes through the electrodes and the dielectric mat and the first and second porous electrodes have a sufficiently high potential difference to facilitate the creation of an induced electrostatic field of at least approximately 1000 V/cm within the dielectric mat, whereby the fluid stream passing through the dielectric mat would be subjected to electrostatic forces that are substantial enough to cause at least some of the particulates within the stream to adhere to the fibers of the dielectric mat.

17. An electrostatic filter as recited in claim 16 wherein a cross section of the fibers has a plurality of distinct regions of small transversal radius of curvature along its perimeter.

18. An electrostatic filter as recited in claim 16 wherein the electrodes are insulated and at least one of the electrodes has a conductive material disposed over at least a portion of the insulation that faces the dielectric mat.

19. An electrostatic filter suitable for collecting aerosol particulates carried in a fluid stream passing through the electrostatic filter, the electrostatic filter comprising:

a first electrode formed from a conductive material;

a dielectric mat formed from a high porosity non-woven fiber having pores that have a void fraction of at least 97%, wherein the fibers have a maximum cross sectional thickness that is less than about 50 microns and wherein the dielectric mat has a tortuosity of at least 1.7; and a second electrode formed from a conductive material, the first and second electrodes being arranged such that in operation a fluid stream to be filtered passes through the electrodes and the dielectric mat and the electrodes may be used to create an induced electrostatic field of at least approximately 1000 V/cm within the dielectric mat, whereby the stream passing through the dielectric mat is subjected to electrostatic forces that are substantial enough to cause at least some of the particulates within the stream to adhere to the fibers of the dielectric mat.

* * * * *